United States Patent [19]

Zaiger

[11] Plant 4,107

[45] Sept. 20, 1977

[54] NECTARINE TREE

[76] Inventor: Chris Floyd Zaiger, 537 Rosemore Ave., Modesto, Calif. 95351

[21] Appl. No.: 709,614

[22] Filed: July 28, 1976

[51] Int. Cl.[2] ..... A01H 5/03

[52] U.S. Cl. ..... Plt./41

[58] Field of Search ..... Plt./41

*Primary Examiner*—Robert E. Bagwill

[57] ABSTRACT

A variety of nectarine tree which is of large size, vigorous, upright in growth; the tree being very productive and regular bearer of large size, late maturing, clingstone fruit having firm yellow flesh and yellow skin color substantially overspread with red.

1 Drawing Figure

ORIGIN OF THE VARIETY

The new variety of nectarine tree was originated by me in my experimental orchard near Modesto, Calif. as a second generation seedling from a cross between Red Grand Nectarine (U.S. Plant Pat. No. 1,060) and a late maturing nectarine seedling of unknown parentage.

ASEXUAL REPRODUCTION OF THE VARIETY

I maintained the selection under careful and continual observation, during which time I recognized its distinct and desirable characteristics described above and selected the variety for reproduction. The present variety was asexually propagated by grafting and budding, as performed at Modesto, California, shows that said characteristics described above proved to be identical to original nectarine tree.

SUMMARY OF THE VARIETY

The present variety of nectarine tree is of large size, vigorous, upright in growth and a productive and regular bearer of large size, clingstone fruit having firm, yellow flesh and yellow skin overspread with a high degree of red; the fruit ripening approximately with Late Le Grand Nectarine (U.S. Plant Pat. No. 1,035).

The present variety of nectarine tree is further characterized as to novelty as having increased productivity and the ability to size a large number of fruit per tree. The fruit colors two to three weeks before ripening; has a higher degree of red skin color than other late fruiting nectarines.

DESCRIPTION OF THE DRAWING

The accompanying photographs show typical specimens of the foliage and fruit of my new variety with upper and lower surfaces of the foliage being illustrated and exterior and a sectional view of the fruit being shown. The illustrations were taken shortly after being picked at maturity (shipping ripe) and the colors are as nearly true as reasonably possibly in a color representation of this type.

DESCRIPTION OF THE VARIETY

The following is a detailed description of the foliage and fruit of my new variety, as based upon observations of specimens grown at Modesto, Calif., with color terminology in accordance with Reinhold Color Atlas by A. Kornerup and J. H. Wanscher.

Tree:
- *Size.*—Large.
- *Vigor.*—Vigorous.
- *Growth.*—Upright.
- *Shape.*—Normally pruned to vase form.
- *Production.*—Productive.
- *Bearing.*—Regular.

Trunk:
- *Size.*—Medium to stocky.
- *Texture.*—Shaggy.

Branches:
- *Size.*—Medium stocky.
- *Texture.*—Smooth to medium rough.
- *Color.*—New growth — reddish brown; Old growth — brown to greyish.
- *Lenticels.*—Medium quantity.

Leaves:
- *Size.*—Large; Average length — 6½" to 8½"; Average width — 1½" to 2¼".
- *Texture.*—Smooth
- *Petiole.*—Medium length.
- *Glands.*—Reniform; Number varies from 2 to 6; Average number 4.
- *Color.*—Upper surface — greyish green (30-E-6) to dark green (30-F-7). Lower surface — greyish green (30-D-6) to green (30-D-7). Heavy midrib on under side yellowish green (30-C-8).

Flower buds:
- *Size.*—Large.
- *Length.*—Medium.

Flowers:
- *Date of first bloom.*—Feb. 22, 1976.
- *Date of last bloom.*—Mar. 1, 1976.
- *Size.*—Large — showy.
- *Pollen.*—Present.
- *Color.*—Pink.

Fruit:
- *Maturity when described.*—Hard ripe.
- *Date of first picking.*—Aug. 10, 1975.
- *Date of last picking.*—Aug. 17, 1975
- *Size.*—Large; Average diameter axially 3" to 3½"; Average transversely in suture plane — 2⅞" to 3½".
- *Form.*—Globose. Slightly flattened at stem end.
- *Suture.*—Shallow — extends from base to apex with slight depression beyond pistil point.
- *Ventral Surface.*—Rounded and only very slightly lipped.
- *Cavity.*—Rounded; Average depth — ⅜" to ½"; Average breadth — 15/16" to 1⅛".
- *Apex.*—Varied from retuse to very slight pistil point.

Skin:
- *Thickness.*—Thick to medium.
- *Texture.*—Tough to medium.

*Tendency to Crack.*—None.
*Down.*—Wanting.
*Color.*—Yellow ground color (4-A-8) to (4-B-8) almost entirely overspread with red (9-A-8) to (10-B-8).

Flesh:
*Juice.*—Moderate.
*Texture.*—Firm, meaty.
*Ripens.*—Even.
*Flavor.*—Sub-acid to mild.
*Aroma.*—Very little.
*Eating quality.*—Good.
*Color.*—Yellow (4-A-7) to (5-A-6).

Stone:
*Type.*—Clingstone.
*Size.*—Medium; Average length — 1¼"; Average width — ⅞"; Average thickness ½".
*Form.*—Ovoid.
*Base.*—Straight to slightly oblique.
*Apex.*—Acute.
*Sides.*—Nearly equal.
*Surface.*—Pitted throughout.
*Ridges.*—Rounded.
*Tendency to split.*—Slight.

*Color.*—Light brown.
Use: Dessert. Market — local and long distance shipping.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, bearing large, yellow flesh, clingstone fruit approximately the same maturity season as Late Le Grand Nectarine (U.S. Plant Pat. No. 1,035), but being an improvement over other nectarines in this maturity season by producing fruit with a higher degree of red skin color. The nectarine tree is further characterized for heavy production, regular bearing of large firm high colored fruit, with long distance shipping quality.

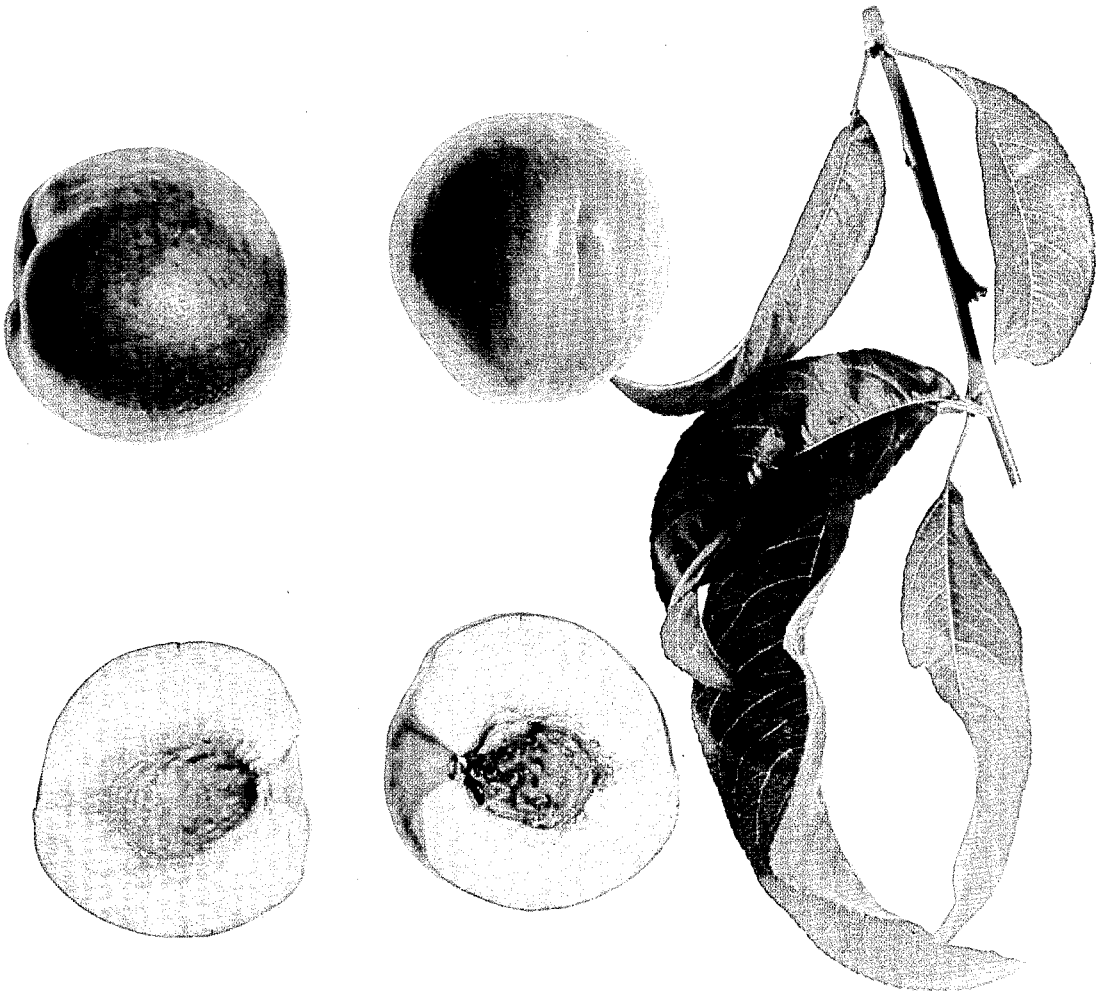

* * * * *